United States Patent [19]

Hagan et al.

[11] Patent Number: 5,490,955
[45] Date of Patent: Feb. 13, 1996

[54] CLEANSING COMPOSITIONS BASED ON $C_{10}$-$C_{16}$ ACYL LACTYLATE

[75] Inventors: Desmond B. Hagan; Peter Carter, both of South Wirral, England

[73] Assignee: Elizabeth Arden Company, Division of Conopco, Inc., New York, N.Y.

[21] Appl. No.: 410,651

[22] Filed: Mar. 24, 1995

Related U.S. Application Data

[63] Continuation of Ser. No. 23,186, Feb. 25, 1993, abandoned.

[30] Foreign Application Priority Data

Feb. 27, 1992 [GB] United Kingdom ............... 9204175

[51] Int. Cl.⁶ ............... C11D 1/37; C11D 1/04; C11D 1/28; A61K 7/06
[52] U.S. Cl. ............... 252/554; 252/89.1; 252/173; 252/174.23; 252/546; 252/547; 252/555; 252/DIG. 5; 252/DIG. 13; 424/70.19; 424/70.22; 424/70.24
[58] Field of Search ............... 252/DIG. 5, DIG. 13, 252/546, 527, 89.1, 547, 528, 174.23, 173, DIG. 7, 554, 555, 535, 536; 424/70.19, 70.22, 70.24

[56] References Cited

U.S. PATENT DOCUMENTS

| | | | |
|---|---|---|---|
| 3,728,447 | 4/1973 | Osipow et al. | 424/70 |
| 3,857,960 | 12/1974 | Mackles | 252/153 |
| 4,029,606 | 6/1977 | Isa et al. | 252/89.1 |
| 4,198,311 | 4/1980 | France et al. | 252/89.1 |
| 4,486,328 | 12/1984 | Knott et al. | 252/117 |
| 4,758,376 | 7/1988 | Hirota et al. | 252/DIG. 5 |
| 4,761,279 | 8/1988 | Khalil et al. | 424/73 |
| 4,846,991 | 7/1989 | Suzue et al. | 252/89.1 |
| 4,946,832 | 8/1990 | Goode et al. | 424/69 |
| 5,002,680 | 3/1991 | Schmidt et al. | 252/DIG. 5 |
| 5,015,471 | 5/1991 | Birtwistle et al. | 252/DIG. 16 |
| 5,078,991 | 1/1992 | Birtwistle et al. | 252/DIG. 5 |
| 5,093,112 | 3/1992 | Birtwistle et al. | 252/DIG. 5 |
| 5,102,572 | 4/1992 | Borland et al. | 252/DIG. 5 |
| 5,139,781 | 8/1992 | Birtwistle et al. | 252/DIG. 5 |

FOREIGN PATENT DOCUMENTS

| | | |
|---|---|---|
| 0194097 | 9/1986 | European Pat. Off. . |
| 0224796 | 6/1987 | European Pat. Off. . |
| 0371803 | 6/1990 | European Pat. Off. . |
| WO92/06669 | 4/1992 | WIPO . |
| WO92/08439 | 5/1992 | WIPO . |
| WO92/21320 | 12/1992 | WIPO . |

OTHER PUBLICATIONS

European Search Report EP 93 30 1399, Jun. 11, 1993.

*Primary Examiner*—Paul Lieberman
*Assistant Examiner*—A. Hertzog
*Attorney, Agent, or Firm*—Milton L. Honig

[57] ABSTRACT

The invention provides a cleansing composition, which comprises in addition to water, (a) from 10 to 30% by weight of one or more $C_6$ to $C_{16}$ acyl lactylates and (b) from 5 to 25% by weight of one or more co-surfactants, such as acyl taurates, isethionates, sarcosinates and sulphosuccinates. The cleansing compositions are primarily intended to be used as personal washing products, such as facial wash foams, bath foams and hair shampoos.

8 Claims, No Drawings

CLEANSING COMPOSITIONS BASED ON $C_{10}$–$C_{16}$ ACYL LACTYLATE

FIELD OF THE INVENTION

This is a continuation divisional application of Ser. No. 08/023,186 filed Feb. 25, 1993, now abandoned.

The invention relates to cleansing compositions. In particular, the invention is concerned with very mild and high foaming cleansing compositions suitable for cleansing the skin and hair.

BACKGROUND TO THE INVENTION AND PRIOR ART

The most widely used anionic surfactants in cleansing compositions are alkyl sulphates, polyoxyethylene alkyl sulphates and alkyl benzene sulphonates. These compounds are known to have a good foaming and deterging power. Due to their harshness, however, they are not desirable as components for cleansing compositions topically applied to human skin and hair. Their damaging effect particularly where young, tender or damaged skin is involved, has been the subject of intense study for many years.

On the other hand milder surfactants often suffer from the draw-back that they do not provide high foam which is very important for the consumer. Therefore, there is a strong need for products which are not only very mild but also possess an excellent foaming power.

U.S. Pat. No. 3,728,447 (C. J. Patterson) discloses hair shampoo compositions containing fatty acid lactylates or glycolates. While the cleaning action of shampoos based on the fatty acid lactylates is satisfactory the foam is minimal. In order to achieve higher foaming action it is described to include harsh detergents such as sodium lauryl sulphate or triethanolamine lauryl sulphate. When the lactylates are used in conjunction with such a booster detergent the quantity of the lactylates present in the composition is reduced down to about 1 to 2% by weight.

EP-A-224 796 (Kao) describes a detergent composition comprising (a) a phosphate surfactant and (b) an acyl lactylate having an acyl group containing 12 to 18 carbons atoms. The detergent composition is said to have excellent foaming characteristics as well as excellent detergency and mildness to the skin and hair. It is taught that these characteristics are only achievable if the acyl lactylate is used in an amount of not more than 5% by weight and preferably not more than 3% by weight of the composition.

U.S. Pat. No. 4,761,279 (Eastman Kodak) describes shaving cream formulations comprising salts of acyl lactylates, saturated monoglycerides, propyleneglycol mono esters and humectants.

U.S. Pat. No. 4,946,832 (RITA Corporation) describes cosmetic base compositions comprising 1 to 15% by weight sucrose fatty acid ester, 3 to 45% by weight acyl lactylate or its alkali metal salts and solvent. The compositions promote wound healing and reduces skin dryness. Foaming properties of the compositions are not reported.

Applicants in their search for mild cleansing compositions, in particular for cleansing human skin or hair, with the added attribute that full lather is produced, have unexpectedly discovered that a narrow range of acyl lactylates in combination with specific co-surfactants provide the desired effects when used in particular amounts. The compositions so obtained are capable of producing a superior lather and accordingly have great consumer appeal. Also, the compositions are so mild that they can safely be used for cleansing the skin and the hair and other more delicate skin areas.

DEFINITION OF THE INVENTION

Accordingly, the invention provides a cleansing composition which comprises, in addition to water, (a) from 10 to 35% by weight of one or more acyl lactylate(s) of the following structure (1)

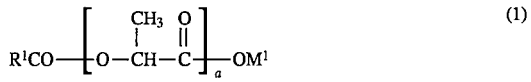

where $R^1CO$ represents a $C_6$ to $C_{16}$ acyl radical; a is an integer from 1 to 3; $M^1$ represents hydrogen or a counterion chosen from alkali metal, ammonium or a substituted ammonium group having one or more $C_1$ to $C_3$ alkyl or hydroxy alkyl group(s); and (b) from 5 to 25% by weight of one or more co-surfactant(s) chosen from the following compounds (A) to (O):

(A) N-methyl-N-acyl taurates of the following structure (2)

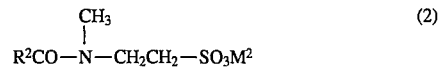

where $R^2CO$ represents a $C_{10}$ to $C_{18}$ acyl group; and $M^2$ is as $M^1$ in structure (1);

(B) Acylisethionates of the following structure (3)

$$R^3CO\text{—}OCH_2CH_2\text{—}SO_3M^3 \qquad (3)$$

where $R^3CO$ represents a $C_{10}$ to $C_{18}$ acyl group; and $M^3$ is as $M^1$ in structure (1);

(C) Alkylesters of ω-sulphonated carboxylic acids of the following structure (4)

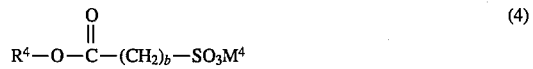

where $R^4$ represents a $C_{10}$ to $C_{18}$ alkyl group; $M^4$ is as $M^1$ in structure (1); and (b) is an integer from 1 to 3;

(D) Fatty acylamido polyoxyethylene sulphates of the following structure (5)

$$R^5CO\text{—}NH\text{—}(CH_2CH_2O)_c\text{—}SO_3M^5 \qquad (5)$$

where $R^5CO$ represents a $C_{10}$ to $C_{18}$ acyl group; $M^5$ is as $M^1$ in structure (1); and c is an integer from 1 to 10;

(E) Fatty acid polyglyceride sulphates of the following structure (6)

$$R^6CO\text{—}O\text{—}(CH_2\text{—}CHOH\text{—}CH_2O)_d\text{—}SO_3M^6 \qquad (6)$$

where $R^6CO$ represents a $C_{10}$ to $C_{18}$ acyl group; $M^6$ is as $M^1$ in structure (1); and d is an integer from 1 to 4;

(F) Mono substituted sulphosuccinates of the following structures (7a) or (7b)

where $Z^7$ is chosen from the following groups (i) to (iii):

(i) $R^8CO-NH-(CH_2CH_2O)_e-$, where $R^aCO$ represents a $C_{10}$ to $C_{18}$ acyl group; and e is an integer from 1 to 10;

(ii) $R^b-O-(CH_2CH_2O)_f-$, where $R^b$ represents a $C_{10}$ to $C_{18}$ alkyl group; and f is an integer from 1 to 10;

(iii) $R^c-O-$, where $R^c$ represents a $C_{10}$ to $C_{18}$ alkyl group; and $X^7$ and $Y^7$ are independently from each other chosen from the counterions represented by $M^1$ in structure (1);

(G) Mono substituted phosphates of the following structure (8)

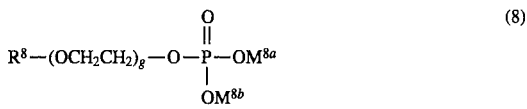

where $R^8$ represents a $C_{10}$ to $C_{18}$ alkyl group; $M^{8a}$ and $M^{8b}$ are independently from each other chosen from the group of species represented by $M^1$ in structure (1); and g is an integer from 0 to 3;

(H) Alkyl poly(ethylene glycol) acetates of the following structure (9)

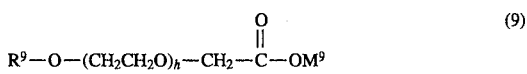

where $R^9$ represents a $C_{10}$ to $C_{18}$ alkyl group; $M^9$ is as $M^1$ in structure (1); and h is an integer from 1 to 10;

(I) Salts of N-acyl α-amino acids of the following structure (10)

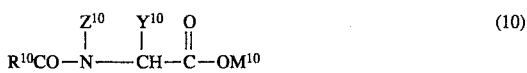

where $R^{10}CO$ represents a $C_{10}$ to $C_{18}$ acyl group; $Z^{10}$ represents H or $C_1$ to $C_2$ alkyl; $Y^{10}$ represents H, $C_1$ to $C_3$ alkyl or $C_1$ to $C_3$ alkyl substituted with a COOH group; and $M^{10}$ is chosen from the counterions represented by $M^1$ in structure (1);

(K) Alkyl polyglucosides of the following structure (11)

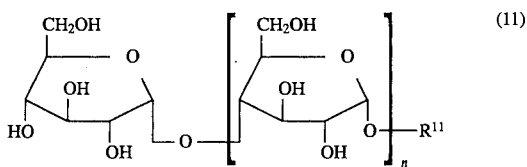

where $R^{11}$ represents a $C_{10}$ to $C_{14}$ alkyl group; and n is an integer from 1 to 3;

(L) Poly(oxyalkylene) fatty alkyl ether of the following structure (12)

where $R^{12}$ represents a $C_8$ to $C_{18}$ alkyl group; $Z^{12}$ is a $C_2$ or $C_3$ alkylene group; and p is an integer from 1 to 10;

(M) N-substituted betaines of the following structure (13)

where $Z^{13}$ represents (i) a $C_{10}$ to $C_{18}$ alkyl group; or (ii) a $R^{13}CO-NH-(CH_2)_3$ group, where $R^{13}CO$ represents a $C_{10}$ to $C_{18}$ acyl group;

(N) Sultaines of the following structure (14)

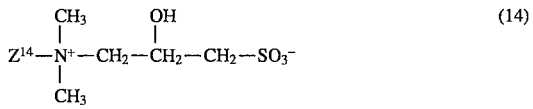

where $Z^{14}$ represents a $C_{10}$ to $C_{18}$ alkyl group or a $C_{10}$ to $C_{18}$ acyl amido group;

(O) Alkyl amphocarboxylates of the following structure (15)

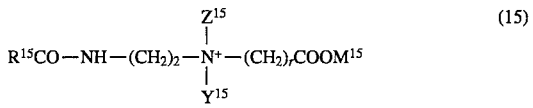

where $R^{15}CO$ represents a $C_{10}$ to $C_{18}$ acyl group; $Z^{15}$ and $Y^{15}$ are independently from each other chosen from H, $CH_2CH_2OH$ or $(CH_2)_rCOO^-$; r is 1 or 2; and $M^{15}$ is as $M^1$ in structure (1);

the composition having a foam height of more than 130 mm, as measured by the foam height test described herein.

DISCLOSURE OF THE INVENTION

The Acyl lactylate

The composition according to the invention comprises from 10 to 35% by weight of one or more acyl lactylate(s) of the following structure (1)

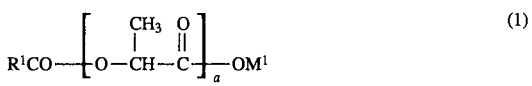

where $R^1CO$ represents a $C_6$ to $C_{16}$ acyl radical; a is an integer from 1 to 3; $M^1$ represents hydrogen or a counterion chosen from alkali metal, ammonium or substituted ammonium group having one or more $C_1$ to $C_3$ alkyl or hydroxy alkyl group (s).

Examples of acyl lactylates having the above structure (1) include:

Sodium lauroyl monolactylate
Sodium myristoyl monolactylate
Sodium decanoyl monolactylate
Potassium dodecanoyl monolactylate
Potassium dodecanoyl dilactylaate
Sodium myristoyl dilactylate
Sodium lauroyl dilactylate
Lauroyl dilactylic acid
Palmitoyl dilactylic acid
Triethanolammonium dodecanoyl monolactylate
Ammonium decanoyl monolactylate, and
Triethanolammonium decanoyl monolactylate.

The preferred acyl group $R^1CO$ is a $C_{10}$ to $C_{14}$ acyl group.

Preferred examples for $M^1$ include sodium, potassium, ammonium and triethanolammonium.

The amount of the acyl lactylate present in the composition according to the invention is preferably from 15 to 30%, most preferred from 20 to 30% by weight of the composition.

The Co-surfactant

The composition according to the invention further comprises one or more co-surfactant(s) in an amount from 5 to 25% by weight of the composition. The co-surfactant is chosen from the compounds (A) to (O) described hereinafter.

The preferred amount of the co-surfactant present in the composition is from 10 to 25% by weight.

The co-surfactants useful in the present invention are not only very mild but also result in high foaming compositions when combined with the acyl lactylate in the specified amounts.

The following compounds are suitable as co-surfactant in the cleansing composition according to the invention.

(A) N-methyl-N-acyl taurates, having the following structure (2)

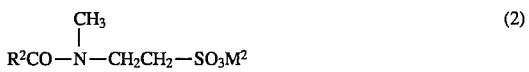

where $R^2CO$ represents a $C_{10}$ to $C_{18}$ acyl group; and $M^2$ is as $M^1$ in structure (1).

Preferred examples for taurates having the structure (2) include:

Sodium N-methyl-N-cocoyl taurate, e.g. available as Diapon K from Nippon Oil and Fats, Sodium N-methyl-N-lauroyl taurate, e.g. available as Diapon LM from Nippon Oils and Fats, Sodium N-methyl-N-myristoyl taurate, e.g. available as Nikkol MMT from Nikkol Chemicals.

(B) Acylisethionates, having the structure (3);

$R^3CO$ represents a $C_{10}$ to $C_{18}$ acyl group; and $M^3$ is as $M^1$ in structure (1).

The preferred example for an Acylisethionate having the structure (3) is sodium cocoyl isethionate, e.g. available as Fenopon AC 78 from Rhone Poulenc.

(C) Alkylesters of ω-sulphonated carboxylic acids, having the structure (4);

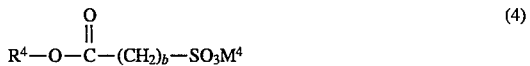

where $R^4$ represents a $C_{10}$ to $C_{18}$ alkyl group; $M^4$ is as $M^1$ in structure (1); and (b) is an integer from 1 to 3.

The preferred example for an Alkylester of a ω-sulphonated carboxylic acid having the structure (4) is sodium lauryl sulphoacetate, e.g. available as Lathanol LAL from Stepan or as Nikkol LSA and Nikkol Chemicals.

(D) Fatty acylamido polyoxyethylene sulphates, having the structure (5);

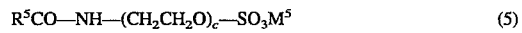

where $R^5CO$ represents a $C_{10}$ to $C_{18}$ acyl group; $M^5$ is as $M^1$ in structure (1); and c is an integer from 1 to 10.

The preferred example for a sulphate having the structure (5) is sodium cocoyl amide EO-3 sulphate, e.g. available as Sunamide C-3 from Nippon Oils & Fats.

(E) Fatty acyl polyglyceride sulphates, having the structure (6);

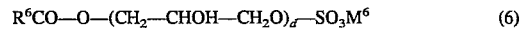

where $R^6CO$ represents a $C_{10}$ to $C_{18}$ acyl group; $M^6$ is as $M^1$ in structure (1); and d is an integer from 1 to 4;

A preferred example for a fatty acyl poly(glyceride) sulphate having the structure (6) is sodium cocoyl monoglyceride sulphate, available from Jan Dekker International.

(F) Mono substituted sulphosuccinates, having the structures (7a) or (7b);

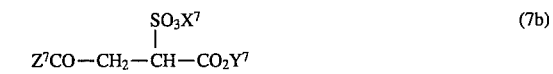

where $Z^7$ is chosen from the following groups (i) to (iii):

(i) $R^aCO-NH-(CH_2CH_2O)_e-$, where $R^aCO$ represents a $C_{10}$ to $C_{18}$ acyl group; and e is an integer from 1 to 10;

(ii) $R^b-O-(CH_2CH_2O)_f-$, where $R^b$ represents a $C_{10}$ to $C_{18}$ alkyl group; and f is an integer from 1 to 10;

(iii) $R^c-O-$, where $R^c$ represents a $C_{10}$ to $C_{18}$ alkyl group; and $X^7$ and $Y^7$ are independently from each other chosen from the counterions represented by $M^1$ in structure (1).

Preferred examples for mono substituted sulphosuccinates represented by the structures (7a) and (7b) include:

Disodium lauroyl amido (EO)-2 to 3 sulphosuccinate e.g. available as Beaulight A-5000 from Sanyo Chemicals, a mixture of Disodium lauryl (PEG)-2 sulphosuccinate and Disodium myristyl (PEG)-2 sulphosuccinate, e.g. available as Beaulight ESS from Sanyo Chemicals, Disodium lauryl (PEG)-2 to 3 sulphosuccinate, e.g. available as Rewopol SBFA 30 from Rewo, and Disodium lauryl sulphosuccinate, e.g. available as Beaulight SSS from Sanyo Chemicals.

The short form (EO)-2 to 3 denotes that, as an average value, 2 to 3 oxyethylene groups are present per molecule sulphosuccinate. On the other hand, the short form (PEG)-2 to 3 stands for the presence of a polyethylene glycol group derived from, as an average value, 2 to 3 ethylene glycol molecules per molecule sulphosuccinate.

(G) Mono substituted phosphates, having the structure (8),

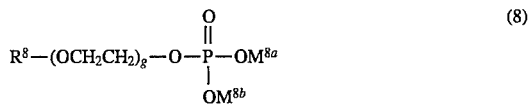

where $R^8$ represents a $C_{10}$ to $C_{18}$ alkyl group; $M^{8a}$ and $M^{8b}$ are independently from each other chosen from the group of species represented by $M^1$ in structure (1); and g is an integer from 0 to 3.

Preferred examples for Mono substituted phosphates having the structure (8) include:

Monosodium monolauryl phosphate, e.g. available as Phosten HLP from Nikkol Chemicals, Monosodium monolauryl (EO)-1 phosphate, e.g. available as Phosten HLP-1 from Nikkol Chemicals, and Monosodium monolauryl (EO)-2 to 3 phosphate, e.g. available as Phosphanol ML 220 from Toho Chemicals.

(H) Alkyl poly(ethylene glycol) acetate, having the structure (9),

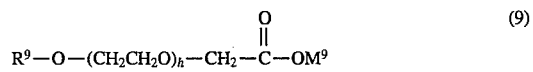

where $R^9$ represents a $C_{10}$ to $C_{18}$ alkyl group; $M^9$ is as $M^1$ in structure (1); and h is an integer from 1 to 10.

Preferred examples for Alkyl (PEG) acetates having the structure (9) include, Sodium Cocoyl PEG-10 acetate, e.g. available as Marlinat CM 105 from Huls, and Sodium tridecyl (PEG)-3 acetate, e.g. available as Beaulight ECA from Sanyo Chemicals.

(I) Salts of N-acyl α-amino acids, having the structure (10);

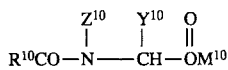

$$R^{10}CO-N\underset{|}{\overset{Z^{10}}{|}}-\underset{}{\overset{Y^{10}}{|}}CH-\overset{O}{\overset{\|}{C}}-OM^{10} \quad (10)$$

where $R^{10}CO$ represents a $C_{10}$ to $C_{18}$ acyl group; $Z^{10}$ represents H or $C_1$ to $C_2$ alkyl; $Y^{10}$ represents H, $C_1$ to $C_3$ alkyl or $C_1$ to $C_3$ alkyl substituted with a COOH group; and $M^{10}$ is chosen from the counteriouns represented by $M^1$ in structure (1).

Preferred examples for salts of N-acyl α-amino acids having the structure (10) include:

Sodium N-lauroyl glutamate, available as Amisoft, LS-11 from Ajinomoto Inc.,

Sodium N-cocoyl glutamate, e.g. available as Amisoft CS-11 from Ajinomoto Inc.,

Triethanolammonium N-cocoyl sarcosinate, e.g. available as Firet KT from Nippon Oil and Fats, Sodium N-decanoyl sarcosinate, Sodium N-lauroyl alaninate, e.g. available as Alaninate LN-30 from Nikkol Chemicals, Sodium N-cocoyl alaninate, Sodium N-cocoyl aspartate, and Sodium N-lauroyl aspartate.

(K) Alkyl poly glucoside, having the structure (11);

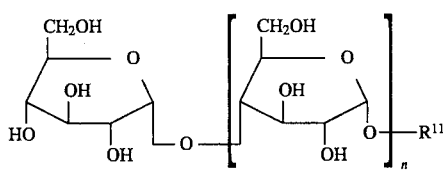

where $R^{11}$ represents a $C_{10}$ to $C_{14}$ alkyl group; and n is an integer from 1 to 3.

Preferred examples for Alkyl poly glucosides having the structure (11) include;

Decyl poly glucoside (n=1.44), e.g. available as Oramix NS10 from Seppic, and $C_9$–$C_{11}$ Alkyl poly glucoside (n=1.4), e.g. available as APG 300 from Henkel.

(L) Poly(oxyalkylene) fatty alkyl ether, having the structure (12), $$R^{12}-O-(Z^{12}O)_pH \quad (12)$$

where $R^{12}$ represents a $C_8$ to $C_{18}$ alkyl group; $Z^{12}$ is a $C_2$ or $C_3$ alkylene group; and p is an integer from 1 to 10.

Preferred examples for a poly(oxyalkylene)-fatty alkyl ether having the structure (12) are (PEG)-6 lauryl ether and (PEG)-6 myristyl ether. A mixture of (PEG)-6 $C_{12}$–$C_{15}$ is available as Dobanol 91-6 from Shell Chemicals.

(M) N-substituted Betaines, having the structure (13);

where $Z^{13}$ represents (i) a $C_{10}$ to $C_{18}$ alkyl group; or (ii) a $R^{13}CO-NH-(CH_2)_3$ group, where $R^{13}CO$ represents a $C_{10}$ to $C_{18}$ acyl group.

Preferred examples for N-substituted Betaines having the structure (13) include:

Lauryl dimethyl betaine, e.g. available as Empigen BB from Albright & Wilson, and cocoamidopropyl betaine, e.g. available as Tegobetaine L7F from Goldschmidt.

(N) Sultaines, having the structure (14);

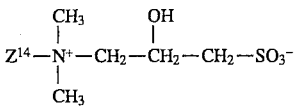

where $Z^{14}$ represents a $C_{10}$ to $C_{18}$ alkyl group or a $C_{10}$ to $C_{18}$ acyl amido group.

A preferred example for a Sultaine having the structure (14) is Cocoamidopropyl hydroxysultaine, e.g. available as Cycloteric BET-CS from Alcolac.

(O) Alkylamphocarboxylates, having the structure (15);

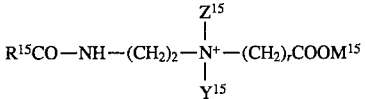

where $R^{15}CO$ represents a $C_{10}$ to $C_{18}$ acyl group; $Z^{15}$ and $Y^{15}$ are independently from each other chosen from H, $CH_2CH_2OH$ or $(CH_2)_rCOO^-$; r is 1 or 2; and $M^{15}$ is as $M^1$ in structure (1).

Preferred examples for Alkylamphocarboxylates having the structure (15) include:

Cocoamphoglycinate e.g. available from GAF,

Wheatgerm amphodiglycinate,

Cocamphodipropionate, e.g. available as Mirataine C2MS from Rhone Poulenc,

Caprylamphodipropionate, e.g. available as Miranol S2MSF from Rhone Poulenc,

Cocoamphoacetate, e.g. available as Nissan Anon GLM-R from Nippon Oils & Fats.

Water

The cleansing composition according to the invention also comprises water. The water will normally be present in an amount of up to 85%, preferably from 10 to 85% by weight of the composition.

Optional Ingredients

The cleansing composition according to the invention can also comprise optional ingredients to modify the physical or chemical characteristics of the composition, e.g. product form, foaming properties, pH-value or shelf life.

Examples for ingredients which can be included in the compositions according to the invention are:

Emollients, such as:

[PEG]-20 Corn Glycerides,

[PEG]-60 Corn Glycerides,

[PEG]-20 Almond Glycerides,

[PEG]-60 Almond Glycerides,

[PEG]-12 Palm Kernel Glycerides,

[PEG]-45 Palm Kernel Glycerides,

[PEG]-20 Evening Primrose Glycerides,

[PEG]-60 Evening Primrose Glycerides,

Ethoxylated (EO)-20 methyl glucoside, also referred to as Methyl gluceth-20

Propoxylated (EO)-10 methyl glucoside.

A group of preferred emollients are poly (oxyalkylene) glycerides mono-substituted with a $C_{10}$ to $C_{18}$ alkyl group and having up to 20 $C_2$ to $C_3$ oxyalkylene moieties per molecule of the glyceride, as an average value.

Especially preferred emollients are Polyoxyalkylene methyl glucosides having, as an average value, up to 20 $C_2$–$C_3$ oxyalkylene moieties per molecule glucoside. These emollients are very beneficial as they impart a soft feeling to the skin and support the ability of the skin to retain moisture. Examples for such Polyoxyalkylene methyl glucosides are available as Glucam E-20 and Glucam P10, respectively, from Amerchol.

Humectants, such as glycerine, sorbitol, sodium 2-pyrrolidone-5-carboxylate, soluble collagen, gelatine, ethoxylated (EO)-20 methyl glucoside, and propoxylated (EO)-10 methyl glucoside.

Preservatives, such as ethanol, benzoic acid, sodium benzoate, sorbic acid, alkali metal halides;

PH controlling agents, such as Sodium hydroxide, Citric acid, Triethanolamine, Potassium hydroxide, Amino Sorbitol. The pH controlling agents are preferably present in an amount sufficient to adjust the composition to a pH value in the range of 5.5 to 8.5.

Propellants, such as fluorochloro hydrocarbons, propane, butane, isobutane, dimethyl ether, carbon dioxide, nitrous oxide;

Foam modifying agents, such as cationic polymers, especially quaternised ammonium hydroxy ethyl cellulose polymers, e.g. available as polyquaternium-24 or polyquaternium-10. These polymers make the foam creamier and richer.

Further Optional Ingredients

The composition according to the invention can also contain other optional agents, that is ingredients other than the main ingredients already defined which are conventionally employed in cleansing compositions, such as thickeners.

USE OF THE COMPOSITION

The cleansing composition according to the invention is primarily intended as a personal washing product for cleansing the face. It can also be used for washing the hair as well as the whole body. The composition according to the invention is preferably used as facial cleanser, facial wash foam, hair shampoo, body shampoo, bath foam or shaving cream. Due to the high detergency provided by the composition it is also possible to use it in non-cosmetic applications, such as a household cleanser, carpet cleanser or detergent for tableware.

The following procedure is an example for the use of the cleansing composition according to the invention; a small quantity, for example from 1 to 5 ml, of the composition is either rubbed between the hands, together with water together to form a foam which is then used for washing or applied via a sponge to the area to be cleansed, or the foam is generated directly on that area. The foam is subsequently rinsed away with clean water.

The cleansing composition according to the invention can take the form of a liquid or gel, intended to be dispensed from a capped container such as a bottle, roll-on applicator or tube, or a pump-operated or propellant-driven aerosol dispenser. The composition can also take the form of a solid, such as a stick or a bar or tablet intended to be used for washing instead of a conventional soap bar.

Foaming Properties of the Composition

Although the composition according to the invention does not include harsh surfactants, as are found in conventional cleansing compositions, its foaming power is excellent. This is shown by the foam-heights measured by the Foam-Height Test described hereinafter.

Foam-Height Test

The test-method which has been used to assess the foaming power of the cleansing compositions according to the invention is the ASTM D 1173-53 test, also referred to as Ross-Miles test, and described in J. Ross and G. D. Miles, American Society for Testing Materials, 1953, pages 644–646. The test has been carried out at a temperature of 20° C. by using an aqueous test solution of 0.3% by weight acyl lactylate and 0.1% by weight co-surfactant. This is a realistic concentration of the cleansing composition according to the invention when used by the consumer, e.g. when topically applied on the face or body together with water to generate the desired foam. The pH value of the test solution has been adjusted to a pH of 7.5 by addition of aqueous sodium hydroxide solution.

The following Table I shows the foam heights obtained by using various cleansing compositions according to the invention. In any case the acyl lactylate was a mixture of 70% by weight sodium lauroyl lactylate and 30% by weight myristoyl lactylate. This mixture is available under the trade name Pationic 138C from RITA Patterson. The foam height measured for this mixture without added co-surfactant is quoted as experiment (27).

TABLE I

| Co-surfactant | Foam-height (mm) |
| --- | --- |
| (1) Sodium N-methyl-N-cocoyl taurate | 193 |
| (2) Sodium N-methyl-N-lauroyl taurate | 198 |
| (3) Sodium N-methyl-N-myristoyl taurate | 193 |
| (4) Triethanolammonium N-cocoyl sarcosinate | 210 |
| (5) Sodium N-cocoyl glutamate | 165 |
| (6) Sodium cocoyl isethionate | 185 |
| (7) Sodium mono lauryl phosphate | 180 |
| (8) Sodium mono lauryl [EO]-1 phosphate | 160 |
| (9) Sodium mono lauryl [EO]-2 to 3 phosphate | 190 |
| (10) Sodium cocoyl [PEG]-10 acetate | 180 |
| (11) Sodium tridecyl [PEG]-3 acetate | 155 |
| (12) Sodium N-lauroyl alaninate | 172 |
| (13) Sodium lauryl sulphoacetate | 194 |
| (14) Sodium cocoyl amido [EO]-3 sulphate | 190 |
| (15) Disodium lauroyl amido [EO]-2 to 3 sulphosuccinate | 148 |
| (16) Disodium lauryl sulphosuccinate | 175 |
| (17) Disodium lauryl [PEG]-2 to 3 sulphosuccinate | 170 |
| (18) Mixture of Disodium lauryl/myristyl [PEG]-2 sulphosuccinate | 180 |
| (19) Sodium cocoyl mono glyceride sulphate | 158 |
| (20) Decyl polyglucoside (N* = 1.44) | 170 |
| (21) $C_9$—$C_{11}$ Alkyl polyglucoside (n* = 1.4) | 172 |
| (22) [PEG]-6 $C_{12}$—$C_{15}$ fatty alkyl ether | 168 |
| (23) N-lauryl dimethyl betaine | 180 |
| (24) Cocoamidopropyl betaine | 170 |
| (25) Cocoamphodipropionate | 165 |
| (26) Cocoamphoacetate | 173 |
| (27) — | 125 | n* - degree of polymerisation, cf. structure (11)

It can be seen from experiment (27) that all the co-surfactants used in experiments (1)–(26) enhance the foam height of the acyl lactylate mixture Pationic 138C to some degree. In particular, taurates having the structure (2), sarcosinates having the structure (10), sulphosuccinates, having the structures (7a) or (7b) and isethionates having the structure (3) are capable of increasing the foam height drastically.

The components of the composition and their amounts are chosen in such a manner that the cleansing composition according to the invention has a foam height of more than 130 mm, as measured by the foam height test carried out under the conditions described above.

Preferably the compositions according to the invention have a foam height of more than 150 mm, more preferred more than 170 mm and most preferred more than 190 mm.

The superiority of the compositions according to the invention as compared to conventional products is shown by the foam heights stated in the following Table II for facial wash foams based on conventional surfactant systems.

Again the Ross-Miles test under the above defined conditions was carried out to assess the respective foam heights. The test solutions were aqueous solutions containing the conventional product at a concentration of 1.0% by weight. The percentages given below for the ingredients of the surfactant systems are based on the weight of the respective product.

TABLE II

| Surfactant-System | Foam Height (mm) |
|---|---|
| (1) 14% cocoyl isethionate | 99 |
| (2) 37% mixture of $C_{18}/C_{16}/C_{14}/C_{12}$ potassium soaps | 76 |
| (3) 36% mixture of $C_{14}/C_{12}$ triethanolammonium soaps | 52 |
| (4) 19% Fatty acyl glutamate, 2% Fatty acyl sarcosinate, 4% $C_{14}/C_{12}$ potassium soap, | 70 |
| (5) 10% nonionic surfactant, 4% ether sulphate, 1.6% Fatty acyl sarcosinate | 114 |
| (6) 30% $C_{18}/C_{14}/C_{12}$ potassium soaps 5% Sodium lauroyl glutamate | 54 |
| (7) 10% Sodium lauryl ethersulphate 4% Cocamidopropyl betaine | 128 |

The above data clearly show that the compositions according to the invention give a much higher foam height than cleansing compositions based on conventional surfactant systems.

Although the cleansing compositions according to the invention comprise high amounts of acyl lactylate, namely from 10 to 30% by weight an excellent foaming power is achieved, as is shown by the data in Table I. This is clearly in contrast to the teaching of the prior art as disclosed in EP-A-224 796 (Kao) that only amounts of less than 5% by weight of acyl lactylate should be included in surfactant systems to obtain mild and high foaming cleansing compositions.

The data given in Table III below show the greater foaming power obtainable by compositions embodying the present invention compared to the prior art described in EP-A-224796. Examples (i) to (viii) in Table III contain the same lactylates in the same amounts as corresponding Examples 2 to 9 in Table 7-1 of EP-A-224796. In each of cases (i) to (viii) a 7:3 mixture of triethanolamine mono:di lauryl phosphate was present at a level of 15 wt %, triethanolamine was added to adjust the pH to 7.5 and demineralised water was used to 100 wt %. As shown in Table III in each case the lactylate content is less than 5 wt % and the foam height, as measured by the Ross-Miles test described above, is less than 130 mm.

TABLE III

| Lactylate present | Foam height (mm) |
|---|---|
| (i) 0.5 wt % stearoyl lactylate | 100 |
| (ii) 2.0 wt % stearoyl lactylate | 100 |
| (iii) 0.5 wt % iso-stearoyl lactylate | 105 |
| (iv) 2.0 wt % iso-stearoyl lactylate | 100 |
| (v) 0.5 wt % lauroyl lactylate | 105 |
| (vi) 2.0 wt % lauroyl lactylate | 115 |
| (vii) 0.5 wt % myristoyl lactylate | 105 |
| (viii) 2.0 wt % myristoyl lactylate | 109 |

In contrast Table IV below gives the foaming power of compositions embodying the present invention. The foaming power was measured by the Ross Miles test described above. In each case the solutions were adjusted to pH 7.5 by addition of 20% aqueous solution of NaOH and were made up to 100% with demineralised water.

TABLE IV

| Surfactant System | Foam Height (mm) |
|---|---|
| (ix) 17 wt % 1:1 Sodium $C_{10}$:$C_{12}$ lactylate 2 wt % Sodium N-myristoyl-N-methyl taurate | 135 |
| (x) 10 wt % 7:3 Sodium $C_{12}$:$C_{14}$ lactylate 5 wt % Disodium lauryl/myristoyl sulphosuccinate | 135 |
| (xi) 15 wt % 7:3 Sodium $C_{12}$:$C_{14}$ lactylate 2 wt % triethanolamine mono:di 7:3 lauryl phosphate | 160 |
| (xii) 17 wt % 7:3 Sodium $C_{12}$:$C_{14}$ lactylate 2 wt % Decyl polyglucoside | 150 |
| (xiii) 17 wt % 7:3 Sodium $C_{12}$:$C_{14}$ lactylate 2 wt % Sodium cocoyl isethionate | 150 |

As can be seen from Table IV each surfactant system embodying the present invention had a foam height above 130 mm.

The superiority of the cleansing compositions according to the invention to conventional compositions comprising less than 10% by weight of acyl lactylate is demonstrated by the data given in the following Table V.

The foam heights were again measured by the Ross-Miles Test conducted under the conditions as defined above.

All percentages given are based on the weight of the respective test solution. All test solutions were adjusted to a pH value of 7.5 by addition of aqueous NaOH solution.

TABLE V

| Test Solutions | Foam Height (mm) |
|---|---|
| (A) 5% lauroyl dilactylic acid 5% Triethanolammonium laury sulphate 5% Coconut diethanolamide to 100% demineralised water | 112 |
| (B) 7% lauroyl dilactylic acid 5% Triethanolammonium laury sulphate 3% Coconut diethanolamide to 100% demineralised water | 119 |
| (C) 9% lauroyl dilactylic acid 1% Triethanolammonium laury sulphate 1% Coconut diethanolamide to 100% demineralised water | 116 |
| (D) 9% lauroyl dilactylic acid 3% Triethanolammonium laury sulphate 1% Coconut diethanolamide to 100% demineralised water | 104 |
| (E) 10% Sodium lauroyl/myristoyl lactylate (Pationic 138 C) 4% Sodium cocoyl isethionate 1% Cocoampho carboxy glycinate to 100% demineralised water | 141 |
| (F) 12% Sodium lauroyl/myristoyl lactylate (Pationic 138 C) 1.5% Sodium N-lauroyl sarcosinate 1.5% Sodium N-methyl-N-cocoyl taurate to 100% demineralised water | 136 |
| (G) 15% Sodium lauroyl/myristoyl lactylate (Pationic 138 C) 2% Sodium laurylamide [EO]-3 sulphate to 100% demineralised water | 136 |

The above data show that, although the compositions according to the invention (E) to (G) are used in amounts of 10% by weight or more, they foam much better than the conventional compositions (A) to (D).

The following examples further illustrate the invention by giving conventionally prepared formulations for different types of cleansing compositions.

EXAMPLES

| Example 1 - Facial Cleanser | wt % |
|---|---|
| Potassium dodecanoyl monolactylate | 15.00 |
| Potassium dodecanoyl dilactylate | 15.00 |
| Disodium lauryl sulphosuccinate | 7.00 |
| Glycerol (Humectant) | 5.00 |
| Sodium chloride (Thickener) | 4.20 |
| Methyl gluceth-20 (Humectant/Emollient) | 3.00 |
| Polyquaternium 10 (Foam modifier) | 0.40 |
| Ethyleneglycol monostearate (Thickener) | 0.40 |
| Preservative | 0.30 |
| Fragrance | 0.30 |
| Citric acid | to pH7.0–7.5 |
| Distilled water | to 100.00 |
| Foam height = 153 mm | |

| Example 2 - Mild Facial Cleanser | wt % |
|---|---|
| Sodium myristoyl dilactylate | 20.00 |
| Sorbitol (Humectant) | 9.00 |
| Sodium cocoyl isethionate | 7.00 |
| Cocoamidopropyl hydroxysulphobetaine | 4.00 |
| Polyoxyethylene [EO]-20 sorbitan monolaurate (Thickener) | 3.00 |
| Hydroxypropyl methylcellulose (Thickener) | 0.20 |
| Preservative | 0.20 |
| Fragrance | 0.10 |
| Citric acid | to pH6.0–6.5 |
| Distilled water | to 100.00 |
| Foam height = 162 mm | |

| Example 3 - Facial Cleanser for Dry Skin | wt % |
|---|---|
| Sodium lauroyl dilactylate | 25.00 |
| Sodium monolauryl phosphate | 10.00 |
| Propylene glycol | 10.00 |
| Polyethyleneglycol (PEG)-150 distearate | 5.00 |
| Preservative | 0.25 |
| Fragrance | 0.20 |
| Citric acid | to pH6.5–7.0 |
| Distilled water | to 100.00 |
| Foam height = 139 mm | |

| Example 4 - Mild Facial Cleanser for Sensitive Skin | wt % |
|---|---|
| Lauroyl dilactylic acid | 20.0 |
| Sodium N-methyl-N-myristoyl taurate | 6.00 |
| Cocoamphoacetate | 3.50 |
| Glycerol (Humectant) | 9.00 |
| Diglycerol (Humectant) | 1.00 |
| PEG-20 almond glycerides (Emollient) | 5.00 |
| Polyquaternium 24 (Thickener, Foam Modifier) | 0.40 |
| Sodium Hydroxide (aq. soln.) | to pH6.0–6.5 |
| Distilled water | to 100.00 |
| Foam height = 150 mm | |

| Example 5 - Liquid Hand Soap | wt % |
|---|---|
| Lauroyl dilactylic acid | 7.50 |
| Palmitoyl dilactylic acid | 7.50 |
| Triethanolammonium N-lauroyl glutamate | 9.00 |
| Cocoamidopropyl betaine | 4.00 |
| Propyleneglycol hydroxy isostearate (Thickener) | 1.00 |
| Trisodium citrate (Thickener) | 7.00 |
| Preservative | 0.26 |
| Fragrance | 0.15 |
| Triethanolamine | to pH7.0–7.3 |
| Distilled water | to 100.00 |
| Foam height = 144 mm | |

| Example 6 - Anti-Acne Facial Cleansing Scrub Gel | wt % |
|---|---|
| Sodium decanoyl monolactylate | 18.00 |
| Sodium N-cocoyl sarcosinate | 6.00 |
| Benzoyl peroxide (70% aq. soln.) | 14.30 |
| Polyoxyethylene (PEG)-20 cetyl ether (Thickener, Emulsifier) | 10.00 |
| Magnesium aluminium silicate (Thickener) | 1.00 |
| Disodium ethylenediamine tetraacetate (Chelating Agent) | 0.20 |
| Sodium Hydroxide | to pH7.0–7.5 |
| Distilled water | to 100.00 |
| Foam height = 135 mm | |

| Example 7 - Hair Shampoo | wt % |
|---|---|
| Triethanolammonium dodecanoyl monolactylate | 21.00 |
| Sodium lauryl (PEG)-10 acetate | 4.00 |
| Cocoamphodipropionate | 3.00 |
| Propylene glycol (Humectant) | 2.50 |
| Sodium chloride (Thickener) | 1.20 |
| Preservative | 0.20 |
| Fragrance | 0.20 |
| Citric acid | to pH6.0–6.5 |
| Distilled water | to 100.00 |
| Foam height = 158 mm | |

| Example 8 - Mild Hair Shampoo | wt % |
|---|---|
| Potassium myristoyl dilactylate | 15.00 |
| Lauryl ethoxylated (EO)-2.5 phosphoric acid | 8.00 |
| Sodium pyrrolidone carboxylate (50% aq. soln.) (Humectant) | 1.00 |
| Sodium chloride (Thickener) | 3.00 |
| Fragrance | 0.24 |
| Preservative | 0.10 |
| Potassium hydroxide (aq. soln.) | to pH6.0–6.5 |
| Distilled water | to 100.00 |
| Foam height = 141 mm | |

| Example 9 - Conditioning Shampoo | wt % |
|---|---|
| Potassium lauroyl monolactylate | 11.00 |
| Sodium lauroylamide polyoxyethylene (EO)-3 sulphate | 4.50 |
| Lauryldimethyl betaine | 4.00 |
| Potassium chloride (Thickener) | 2.50 |
| Dimethicone copolyol (Conditioning agent) | 0.50 |
| Preservative | 0.17 |
| Fragrance | 0.11 |
| Dye | 0.02 |
| Citric acid | to pH6.5–7.0 |
| Distilled water | to 100.00 |
| Foam height = 170 mm | |

| Example 10 - Antidandruff Shampoo | wt % |
|---|---|
| Ammonium decanoyl monolactylate | 14.00 |
| Ammonium decanoyl dilactylate | 4.00 |
| Ammonium lauryl sulphoacetate | 5.00 |
| Zinc Pyrithione (48% aq. soln.) (Anti-fungal | 2.10 |

Example 10 - Antidandruff Shampoo

| agent) | wt % | |
|---|---|---|
| Hydroxypropyl methylcellulose | 1.25 | |
| Magnesium aluminium silicate (Thickener) | 1.00 | |
| Preservative | 0.36 | |
| Fragrance | 0.20 | |
| Dye | 0.03 | |
| Citric acid | to | pH7.0–7.3 |
| Distilled water | to100.00 | |
| Foam height = 150 mm | | |

Example 11 - Body Shampoo

| | wt % | |
|---|---|---|
| Dodecanoyl dilactylic acid | 13.00 | |
| Sodium N-cocoyl alaninate | 4.00 | |
| Lauroamphoglycinaate | 4.00 | |
| (PEG)-80 sorbitan laurate (Thickener) | 3.30 | |
| Disodium ethylenediamine tetraacetate | 0.20 | |
| Preservative | 0.10 | |
| Fragrance | 0.05 | |
| Dye | 0.01 | |
| Citric acid | to | pH7.0–7.5 |
| Distilled water | to100.00 | |
| Foam height = 164 mm | | |

Example 12 - Mild Body Shampoo

| | wt % | |
|---|---|---|
| Triethanolammonium lauroyl monolactylate | 7.50 | |
| Triethanolammonium myristoyl monolactylate | 7.50 | |
| Disodium lauryl (PEG)-2.5 sulphosuccinate | 10.00 | |
| Cocoamidoproyl betaine | 5.00 | |
| Glycerol | 5.00 | |
| Polyoxyethylene (PEG)-45 monostearate (Thickener) | 2.00 | |
| Preservative | 0.35 | |
| Fragrance | 0.35 | |
| Citric acid | to | pH7.0–7.5 |
| Distilled water | to100.00 | |
| Foam height = 165 mm | | |

Example 13 - Liquid Body Shampoo

| | wt % | |
|---|---|---|
| Potassium decanoyl monolactylate | 10.00 | |
| Potassium decanoyl dilactylate | 10.00 | |
| Decyl polyglucoside (n = 1.44) | 5.00 | |
| Glycerol | 5.00 | |
| Trisodium citrate dehydrate (Thickener) | 1.50 | |
| Sodium carboxymethyl cellulose (Thickener) | 1.00 | |
| Citric acid | to | pH7.0–7.5 |
| Distilled water | to100.00 | |
| Foam height = 138 mm | | |

Example 14 - Aerosol Body Shampoo

| | wt % | |
|---|---|---|
| Sodium decanoyl monolactylate | 10.00 | |
| Sodium decanoyl dilactylate | 10.00 | |
| Decyl polyglucoside (n = 1.44) | 5.50 | |
| Glycerol | 2.00 | |
| Trisodium citrate dihydrate | 1.50 | |
| Sodium carboxymethyl cellulose | 1.00 | |
| Preservative | 0.35 | |
| Fragrance | 0.35 | |
| Citric acid | to | pH7.0–7.5 |
| Distilled water | to100.00 | |
| Foam height = 140 mm | | |

95% by weight of the solution obtained by mixing the above ingredients was combined with 5% by weight propellant and then sealed into a container.

Example 15 - Bath Foam Concentrate

| | wt % | |
|---|---|---|
| Lauroyl monolactylic acid | 15.00 | |
| Lauroyl dilactylic acid | 10.00 | |
| Cocoamphopropionate | 5.00 | |
| Sorbitol | 9.00 | |
| Sodium chloride | 6.00 | |
| Sodium carboxymethyl cellulose (Thickener) | 1.00 | |
| Preservative | 0.30 | |
| Fragrance | 0.60 | |
| Chamomile distillate (Anti-inflammatory agent) | 1.00 | |
| Aminosorbitol | to | pH7.0–7.5 |
| Distilled water | to100.00 | |
| Foam height = 165 mm | | |

Example 16 - Mild Bath Foam

| | wt % | |
|---|---|---|
| Sodium myristoyl monolactylate | 18.00 | |
| Sodium myristoyl dilactylate | 6.00 | |
| Sodium lauroyl monoglyceride sulphate | 5.00 | |
| Cocoamidopropyl hydroxysulphobetaine | 4.00 | |
| Preservative | 0.20 | |
| Fragrance | 1.00 | |
| Citric acid | to | pH7.2–7.7 |
| Distilled water | to100.00 | |
| Foam height = 149 mm | | |

Example 17 - Conditioning Bubble Bath

| | wt % | |
|---|---|---|
| Triethanolammonium decanoyl monolactylate | 20.00 | |
| Cocoamphodiacetate | 5.00 | |
| Polyoxyethylene (PEG)-20 cetyl ether | 4.00 | |
| Polyoxyethylene (PEG)-50 stearyl ether | 4.00 | |
| Lauryl methyl gluceth-10 hydroxypropyl diammonium chloride (Conditioner) | 0.50 | |
| Polyquaternium 24 (Thickener) | 0.40 | |
| Citric acid | to | pH7.0–7.5 |
| Distilled water | to100.00 | |
| Foam height = 151 mm | | |

Example 18 - Cleansing Bar

| | wt % |
|---|---|
| Sodium lauroyl dilactylate | 20.00 |
| Sodium myristoyl dilactylate | 15.00 |
| Sodium N-cocoyl glutamate | 15.00 |
| Sodium N-stearoyl aspartate | 10.00 |
| Glycerol | 8.00 |
| Diglycerol | 8.00 |
| Preservative | 0.30 |
| Fragrance | 0.60 |
| Pigment | 0.10 |
| Distilled water | to100.00% |
| Foam height = 175 mm | |

Example 19 - Facial Wash Foam

| | % w/w | |
|---|---|---|
| Sodium lauroyl lactylate | 14.00 | |
| Sodium myristoyl lactylate | 6.00 | |
| Sodium lauryl ethoxy phosphate | 6.00 | |
| Disodium lauryl amido ethoxy sulphosuccinate | 2.00 | |
| Disodium wheatgerm amido PEG-2 sulphosuccinate | 2.00 | |
| Polyquaternium-24 | 0.40 | |
| Glycerol (humectant) | 10.00 | |
| (PEG)-12 palm kernel glycerides (emollient) | 5.00 | |
| Sodium hydroxide solution | to | pH6.8–7.0 |

| Example 19 - Facial Wash Foam | % w/w |
|---|---|
| Distilled water | to 100.00% |
| Foam height = 190 mm | |

| Example 20 - Facial Wash Foam | % w/w |
|---|---|
| Sodium lauroyl lactylate | 14.00 |
| Sodium myristoyl lactylate | 6.00 |
| Sodium cocoyl isethionate | 6.00 |
| Wheatgerm amphodiacetate | 2.00 |
| Cocoamphocarboxy glycinate | 2.00 |
| Polyquaternium-24 | 0.40 |
| Glycerol (humectant) | 10.00 |
| (PEG)-40 almond glycerides (emollient) | 5.00 |
| Sodium hydroxide solution | to pH6.8–7.0 |
| Distilled water | to 100.00% |
| Foam height = 180 mm | |

| Example 21 - Facial wash foam | wt % |
|---|---|
| Sodium lauroyl lactylate | 14.00 |
| Sodium myristoyl lactylate | 6.00 |
| Sodium cocoyl isethionate | 6.75 |
| Monolauryl phosphoric acid | 2.40 |
| Dilauryl phosphoric acid | 0.60 |
| Triethanolammonium N-cocoyl sarcosinate | 1.00 |
| Glycerol | 10.00 |
| Polyquaternium 10 | 0.40 |
| Sodium hydroxide solution | to pH6.8–7.0 |
| Distilled water | to 100.00% |
| Foam height = 185 mm | |

| Example 22 - Facial wash foam | wt % |
|---|---|
| Sodium lauroyl lactylate | 14.00 |
| Sodium myristoyl lactylate | 6.00 |
| Sodium cocoyl isethionate | 6.00 |
| Sodium N-methyl-N-cocoyl taurate | 3.00 |
| Sodium N-cocoyl sarcosinate | 1.00 |
| Glycerol | 10.00 |
| Polyquaternium 10 | 0.40 |
| Sodium hydroxide solution | to pH6.8–7.0 |
| Distilled water | to 100.00% |
| Foam Height - 190 mm | |

We claim:

1. A cleansing composition which comprises, in addition to water, (a) from 15 to 35% by weight of one or more acyl lactylate(s) of the following structure (1)

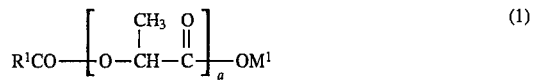

where $R^1CO$ represents a $C_6$ to $C_{16}$ acyl radical; a is an integer from 1 to 3; $M^1$ represents hydrogen or a counterion chosen from alkali metal, ammonium or a substituted ammonium group having one or more $C_1$ to $C_3$ alkyl or hydroxy alkyl group (s); and (b) from 5 to 25% by weight of one or more acylisethionates of the following structure (3)

$$R^3CO\text{—}OCH_2CH_2\text{—}SO_3M^3 \qquad (3)$$

where $R^3CO$ represents a $C_{10}$ to $C_{18}$ acyl group; and $M^3$ is as $M^1$ in structure (1); the composition having a foam height of more than 150 mm, as measured by the Foam Height Test, ASTM D 1173-53.

2. A composition according to claim 1, which has a foam height of more than 170 mm.

3. A composition according to claim 1, which has a foam height of more than 190 mm.

4. A composition according to claim 1, in which the acyl group $R^1CO$ in structure (1) represents a $C_{10}$ to $C_{14}$ acyl radical.

5. A composition according to claim 1, in which the acylisethionate is present in an amount of 10 to 15% by weight.

6. A composition according to claim 1, which further comprises a quaternised ammonium hydroxy ethyl cellulose polymer in a foam modifying effective amount.

7. A composition according to claim 1, which further comprises from 5 to 25% by weight of one or more N-substituted betaines of the following structure (13)

where $Z^{13}$ represents (i) a $C_{10}$ to $C_{18}$ alkyl group; or (ii) an $R^{13}CO\text{—}NH\text{—}(CH_2)_3$ group, where $R^{13}CO$ represents a $C_{10}$ to $C_{18}$ acyl group.

8. Method of cleansing skin or hair using a composition according to claim 1 wherein said composition is applied to said skin or hair.

\* \* \* \* \*